US008506813B2

(12) United States Patent
Alspektor

(10) Patent No.: US 8,506,813 B2
(45) Date of Patent: Aug. 13, 2013

(54) BIDIRECTIONAL TRANSFER OF AN ALIQUOT OF FLUID BETWEEN COMPARTMENTS

(76) Inventor: Beno Alspektor, Kiryat Tivon (IL)

( * ) Notice: Subject to any disclaimer, the term of this patent is extended or adjusted under 35 U.S.C. 154(b) by 733 days.

(21) Appl. No.: 12/664,775

(22) PCT Filed: Jun. 17, 2008

(86) PCT No.: PCT/IL2008/000821
§ 371 (c)(1),
(2), (4) Date: Dec. 15, 2009

(87) PCT Pub. No.: WO2009/001334
PCT Pub. Date: Dec. 31, 2008

(65) Prior Publication Data
US 2010/0181251 A1 Jul. 22, 2010

(30) Foreign Application Priority Data
Jun. 25, 2007 (IL) .......................................... 184183

(51) Int. Cl.
*B01D 11/00* (2006.01)
*B01D 15/00* (2006.01)
*G01N 30/04* (2006.01)
*G01N 30/28* (2006.01)
*G01N 33/544* (2006.01)

(52) U.S. Cl.
USPC ........... 210/638; 210/141; 210/149; 210/175; 210/511; 210/656; 210/774; 210/263; 422/69; 422/509; 422/527; 422/534; 422/112; 436/177; 436/178; 436/518; 436/535

(58) Field of Classification Search
USPC .............. 210/436, 472, 223, 321.6, 335, 464, 210/473, 474, 477, 511, 516, 518, 359, 638, 210/644, 656, 695, 804, 806, 269, 277, 321.69, 210/409, 636, 670, 675–678, 791, 120, 141, 210/149, 188, 263, 660, 690; 73/863.23, 73/863.24; 422/69, 70, 501, 509, 510, 513, 422/527, 534, 535, 544, 545, 549, 550, 105, 422/112, 114; 436/54, 175, 177–180, 161, 436/518, 524, 528, 532, 535; 435/4, 6.1, 435/287.1, 287.2, 287.3, 287.9, 288.6
See application file for complete search history.

(56) References Cited

U.S. PATENT DOCUMENTS 3,231,512 A * 1/1966 Harter ............................. 96/126
3,583,627 A 6/1971 Wilson
3,969,250 A * 7/1976 Farr ............................. 210/359
(Continued)

FOREIGN PATENT DOCUMENTS

DE 3342703 A 5/1984
EP 0338844 A 6/1996
(Continued)

*Primary Examiner* — Joseph Drodge
(74) *Attorney, Agent, or Firm* — Haim M. Factor

(57) ABSTRACT

This invention concerns a method, devices, instrument and program for extraction an ingredient from a liquid sample by bidirectional transfer of an aliquot of fluid between compartments, the method can be applied to a wide variety of laboratory techniques such as; solid phase extraction by filter disc, column chromatography, magnetic separation, diagnostic tests and others, the system is suitable for single or multi sample handling, manual operation or integrated into an automated system, can be used in a lab or in field.

9 Claims, 6 Drawing Sheets

(56) References Cited

U.S. PATENT DOCUMENTS

| | | | | |
|---|---|---|---|---|
| 4,872,988 | A | 10/1989 | Culkin | |
| 4,948,564 | A | 8/1990 | Root et al. | |
| 5,227,137 | A | 7/1993 | Monti et al. | |
| 5,229,297 | A | 7/1993 | Schnipelsky et al. | |
| 5,273,718 | A | 12/1993 | Sköld et al. | |
| 5,464,541 | A * | 11/1995 | Aysta et al. | 210/767 |
| 5,472,605 | A * | 12/1995 | Zuk, Jr. | 210/436 |
| 5,603,899 | A | 2/1997 | Franciskovich et al. | |
| 5,647,994 | A | 7/1997 | Tuunanen et al. | |
| 5,955,351 | A | 9/1999 | Gerdes et al. | |
| 6,068,987 | A | 5/2000 | Dulski et al. | |
| 6,607,662 | B1 | 8/2003 | Ikeda et al. | |
| 6,986,848 | B2 | 1/2006 | Ikeda et al. | |
| 8,105,849 | B2 * | 1/2012 | McDevitt et al. | 436/518 |
| 2001/0055812 | A1 | 12/2001 | Mian et al. | |
| 2002/0025576 | A1 | 2/2002 | Northrup et al. | |
| 2002/0064885 | A1 | 5/2002 | Bedingham et al. | |
| 2002/0086417 | A1 | 7/2002 | Chen | |
| 2002/0097632 | A1 | 7/2002 | Kellogg et al. | |
| 2003/0223913 | A1 * | 12/2003 | Karp et al. | 422/101 |
| 2005/0032238 | A1 * | 2/2005 | Karp et al. | 436/177 |

FOREIGN PATENT DOCUMENTS

| | | | |
|---|---|---|---|
| EP | 0718618 | A2 | 6/1996 |
| GB | 2290244 | A | 12/1995 |
| WO | 9427724 | A | 12/1994 |
| WO | 9626011 | A1 | 8/1996 |
| WO | 9826859 | A1 | 6/1998 |
| WO | 0105510 | A1 | 1/2001 |

* cited by examiner

Figure 6
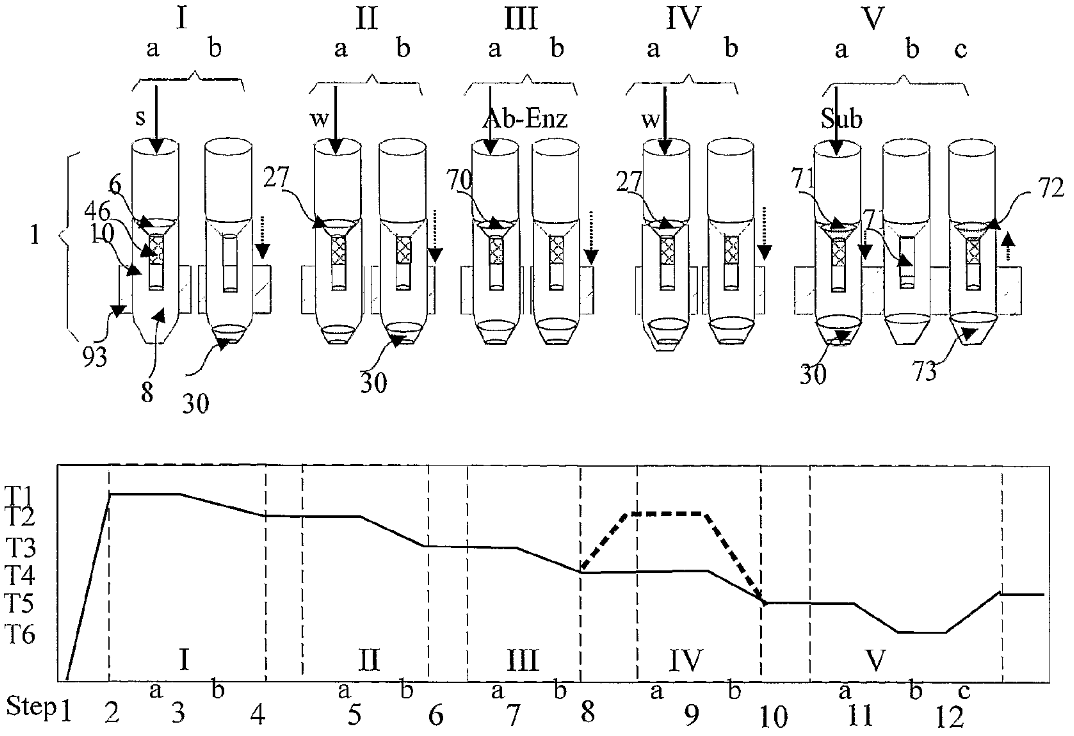
Figure 7
Figure 7-1
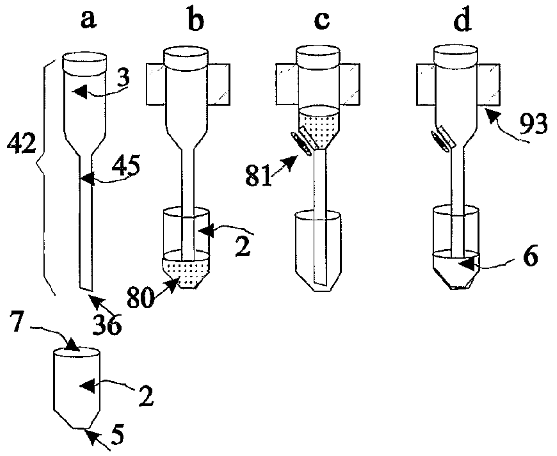
Figure 7-2
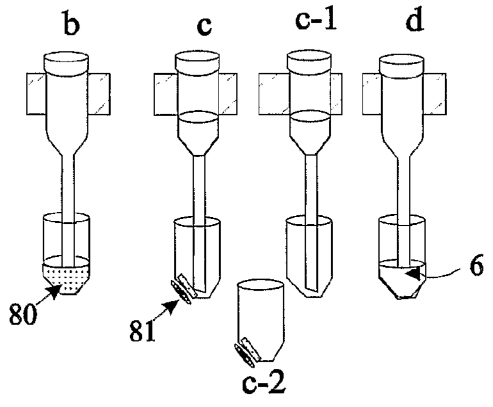

Figure 8
Figure 8-1 Figure 8-2
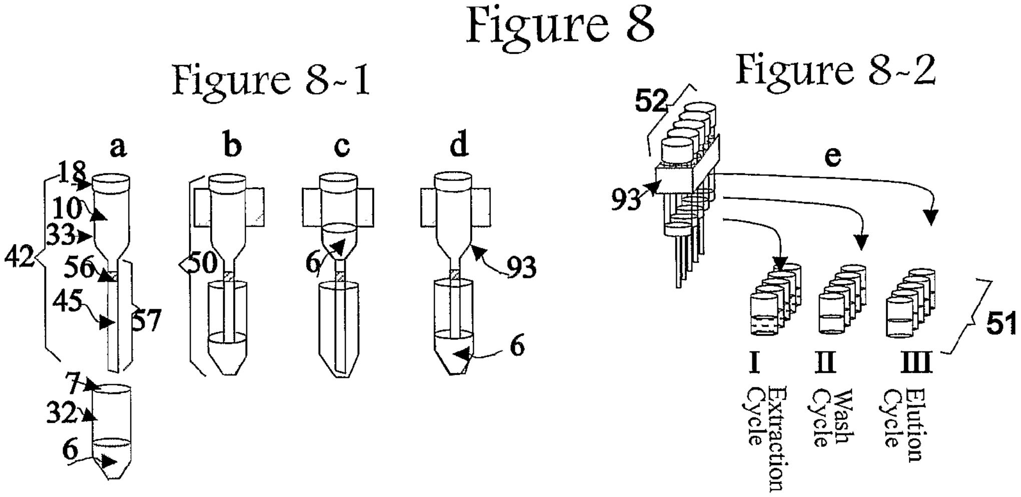
Figure 9
Fig 9-a Fig 9-b
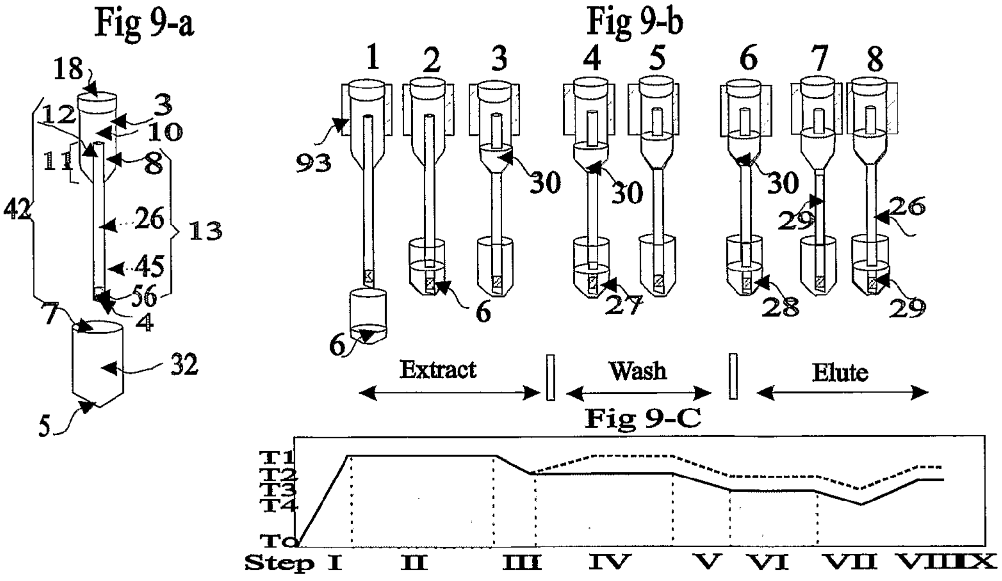

Figure 12

| | Pre-filled reagent cartridge | Pipetting station |
|---|---|---|
| Magnetic separation | PE ☑<br>NE ☑<br>PE-HTS ☐<br>NE-HTS ☐<br>Flexible ☑<br>Mix U-D ☑<br>Mix Air ☐<br>Cartridge ☑<br>Fig7<br>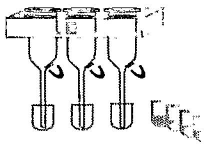 | PE ☑<br>NE ☑<br>PE-HTS ☑<br>NE-HTS ☑<br>Waste ☐<br>Aspiration ☑<br>Flexible ☑<br>Mix U-D ☑<br>Mix Air ☑<br>Decant ☑<br>Hold ☑<br>Fig4<br>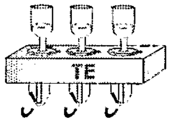<br>PE ☑<br>NE ☐<br>PE-HTS ☑<br>NE-HTS ☐<br>Waste ☑<br>Aspiration ☐<br>Flexible ☑<br>Mix U-D ☐<br>Mix Air ☑<br>Fig3<br>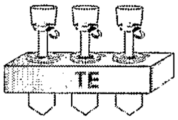 |
| Membrane separation | Fig8<br>PE ☑<br>NE ☑<br>PE-HTS ☑<br>NE-HTS ☑<br>Cartridge ☑<br>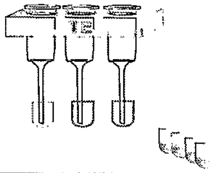 | PE ☑<br>NE ☑<br>PE-HTS ☑<br>NE-HTS ☑<br>Waste ☑<br>Fig1<br>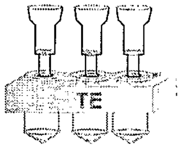 |
| Chromatographic separation | PE ☑<br>NE ☑<br>PE-HTS ☑<br>NE-HTS ☑<br>Cartridge ☑<br>Incubation ☑<br>Fig8<br>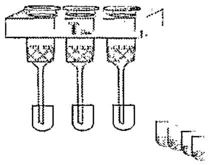 | PE ☑<br>NE ☑<br>PE-HTS ☑<br>NE-HTS ☑<br>Waste ☑<br>Incubation ☑<br>Fig2<br>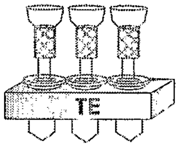 |
| Batch separation | PE ☑<br>NE ☑<br>PE-HTS ☑<br>NE-HTS ☑<br>Flexible ☑<br>Mix U-D ☑<br>Mix Air ☑<br>Cartridge ☑<br>Fig8<br>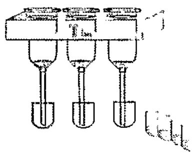 | Fig5<br>PE ☑<br>NE ☑<br>PE-HTS ☑<br>NE-HTS ☑<br>Aspiration ■<br>Incubation ☑<br>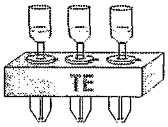 |

PE =Positive Extraction
NE =Negative Extraction
HTS= High troughput system
Mix U-D = mix by cycling of liquid
Mix Air= mix by air bubbles
Waste= Supernatant collected in a waste chamber
Aspiration= Supernatant is aspirated
Flexible = Solid phase can be replaced
Hold= Eluant can be left in device
Decant= decantation

BIDIRECTIONAL TRANSFER OF AN ALIQUOT OF FLUID BETWEEN COMPARTMENTS

The present invention claims the benefit of the PCT/IL2008/00821 patent application filed Jun. 17, 2008, which claims priority to the provisional patent application Ser. No. IL-184183 filed Jun. 25, 2007.

TECHNICAL FIELD

The invention concerns solid phase extraction of an ingredient from a liquid sample, more specifically by using a bi directional transfer of an aliquot of fluid between two compartments assembly, an open compartment in fluidic communication with a closed compartment, by controlling the expansion and contraction of an air pocket in a closed compartment and one of the compartments host the active solid support.

DISCLOSURE

Brief Description of the Invention

This invention concerns a system for extracting an ingredient out of a liquid sample, by using a novel bi directional transfer of an aliquot of fluid between at least two compartments assembly of which; one compartment is closed to the ambient, and the other is open to the ambient. The two compartments communicate via an intermediate semi-permeable, active or passive barrier member, where at least part of the closed compartment contains an air pocket which by cyclic thermal expansion/contraction generates differential pressure between compartments which serves as driving force to push and pull fluid, at least part of the air pocket is always retained in the closed compartment during and after executing each step of the protocol. The closed compartment together with barrier member serves as an automatic valve i.e. prevents fluid flow between compartments under condition of equal pressure in both compartments, yet allows such flow when differential pressure between compartments is established.

In accordance with one preferred embodiment, the air pocket zone of the closed compartment is placed into a thermal member capable of heating and cooling, and the air pocket is being heated or cooled according to a preferred program. The fluid flow between compartments is responding to heating (thermal expansion) or cooling (thermal contraction) of said air pocket, which step establishes a differential pressure between the closed compartment that assumes new pressure, while the pressure in the open compartment remains constant and equal to the ambient pressure, thus the differential pressure between compartments is controlled by regulating the temperature of the entrapped air pocket in the closed compartment. By proper design of the closed compartment and the communicating barrier and by applying the proper temperatures program to the air pocket, the fluid can be force to move from the open compartment to closed compartment or, from closed to the open compartment or in a cycle e.g. from one compartment to the other and then back to the original compartment. The method of the invention can be applied to a wide variety of laboratory techniques involving the transfer of liquid between different compartments such as; filtration, solid phase extraction (SPE) by column chromatography, magnetic bead extraction and separation, assay, pipetting, synchronized addition of a substance to multi tubes and other techniques involving subjecting a liquid sample to various treatments at different times, such as enzymatic treatment, exposure to different temperature, etc. The invention provides a system for simple handling of multiple samples in a direct and accessible environment, i.e. addition of buffer or other ingredients can be accomplished directly into the open compartment, or a pre-filled reagent cartridge can be used, all this operation can be done in a single instrument with minor modification.

Background Art

Many laboratory techniques involve the transfer of liquid sample from one container to a second container, such as solid phase extraction (SPE) in which certain ingredient must be removed from the sample (negative extraction-NE) or where a certain ingredient has to be extracted and purified. (positive extraction-PE). Extraction of DNA for example, from a liquid sample involves moving of liquid from one container having an active solid support such as absorbing membrane, by applying vacuum or, centrifugation force to move the liquid through the membrane into a collecting container, whereby the DNA is retained in the membrane, and after a washing step the collecting container is replace with a new one, and the DNA is eluted by addition of eluting buffer and applying driving force once more.

Other examples are column chromatography, etc., where the sample is place in one chamber (column), and then forced into the chromatographic gel, followed by washing, and finally eluting the appropriate ingredient, at least one step involves the collection of a fraction into a replaced container, each of such techniques calls for a specific instrument and adaptors.

Centrifugation force is time consuming, hard to automat, and involves loading unloading into buckets, balancing the rotor, etc., Pressure or vacuum technique which allow the simultaneous handling of large number of test vessels are available in manifold station where test vessels are arranged in an array and are all inter-connected by a common pathway to pressure or vacuum source, as the case may be. One major drawbacks of such internal fluid connection is that in case of pressure leak even in one vessel due to shortage of liquid, manufacturing defect, improper insertion into the associated aperture and alike, there results a pressure shunt which considerably impairs the normal function of the system Another major drawback of some manifold system is that the separation devices have to be individually plugged into holes in the manifold and blind holes must be capped before applying vacuum or pressure. Another drawback of such techniques is that predetermined aliquot of sample cannot be handles, but rather complete transfer of the sample is accomplished as it involves a continuous flow mechanism. Other drawbacks such as replacing collection tubes and other will be demonstrated when discussed in the specific examples.

U.S. Pat. No. 5,603,899 describe an apparatus, for simultaneously separating multiple samples into their constituents, include a column manifold, which has a plate with a plurality of apertures there through. A plurality of support tubes extend from the plate and each support tube has a passage in communication with one of the apertures. The column manifold also includes a fitting to which vacuum sources can be connected, thus enabling the apparatus to be used with both a centrifuge and a vacuum source. U.S. Pat. No. 5,955,351; describes a self-contained device that integrates nucleic acid extraction, specific target amplification and detection into a single device. The device disclosed is defined by two hollow elongated cylinders, in accordance with this patent, many interventions and internal manipulations are involved for executing the protocol such as: rotating of compartments, opening and closing the cover, applying pressure to the hinged cover, breaking the foil membrane with the knife. US patent 20020025576 relates to an “Integrated sample analysis device” comprises a body having a reaction chamber, a separation region and a transition region connecting the reaction chamber to the separation region. The transition region includes valves for controlling the flow of fluid between the reaction chamber and the separation region. US patent 20020097632 describes a “Bi directional flow centrifugal micro fluidic devices”. by inverting the orientation of the device.

US patent 20020086417 describes a “Sample processing device and method” The processing stations each have a compression member adapted to compress the sample vessel within the opening and thereby move the sample within the sample vessel. The device can be used for PCR processing of nucleic acid samples. US patent 20020064885 relates to “Sample processing devices” for thermal processing of multiple samples at the same time. Comprising; process arrays that include conduits and chambers in fluid communication with the main conduits. The sample processing devices include a deformable seals for forcing fluid movement. U.S. Pat. No. 6,068,978 relates to an “Apparatus and method for transfer of a fluid sample” for amplifying and detecting nucleic acid.

Magnetic methodology: Another technique for extraction of an ingredient from a liquid sample is using magnetic beads. This technology involves mixing of the magnetic solid support with the sample. The magnetic beads may be for example silicon based or are immobilized with an active ingredient, such as Streptavidin which binds Biotinylated nucleic acids and proteins or immobilized with oligo(dT) for mRNA isolation, or with antibody. The paramagnetic beads can be collected by applying a magnetic force. When positive extraction is involved, the supernatant is removed and discarded while the magnetic force is still applied. The paramagnetic beads can be re-suspended in washing solution and magnetic separation is repeated, followed by an elution cycle, one way of handling such protocol is by applying magnetic force when the mixture is aspirated into a tip of pipetting device, the beads are attracted toward the walls of the tip by a magnet, the liquid is forced out of the tip and discarded. U.S. Pat. No. 5,647,994; a method for separating magnetic particles from a solution and transferring them into another solution. U.S. Pat. Nos. 6,607,662 and 6,986,848 describes an Apparatus for purifying nucleic acids and proteins comprising: a plurality of piston pumps; and a plurality of nozzles having disposable tips which are automatically attachable/detachable, followed by discharging the mixtures in the sections simultaneously; and a mechanism for dispensing a desired amount of a second reagent to be used subsequently into a same number of sections of a different container, while the mixing is in progress.

Technical Problem

Summery of some major advantages and drawback of prior technology

Vacuum method: Advantages: free access to upper container. Drawbacks: Shunt effect, flow control needs addition of individual flow adjusting valves, no incubation option, no volume control, only one extraction passage, replacement of collection tube, hard to automat, not suitable for magnetic bead separation Centrifugal method: Advantages: No shunt effect, simple single or multiple samples. Drawbacks: No free access to upper container, hard to automat, no incubation option, no volume control, not suitable for magnetic bead separation Magnetic methodology: Advantages: Extraction in the presence of solid contaminant, easy automation. Drawbacks: Long parking of essential pipettor station during incubation, cross contamination when decantation of multi-well plate.

Technical Solution

This invention propose a unified platform, including method, instrument and devices for extracting ingredient out of a liquid sample using solid phase extraction methodology. The unified platform can be used for any of chromatographic column, magnetic beads, non-magnetic beads or membrane filter. The system is characterized by bi directional transfer of an aliquot of fluid between two compartments assembly of which one compartment is closed to the ambient, and the other is open to the ambient. The two compartments communicate via an intermediate semi-permeable, active or passive barrier member, the closed compartment contains an air pocket which is inserted into a programmable heating/cooling member to control the expansion and contraction of the entrapped air, which in turn generates differential pressure between compartments which serves as driving force to push or pull fluid, be it air, liquid or suspension. By proper design of the closed and open compartments, communicating barrier and solid support and by applying the proper temperatures program to the air pocket, the fluid can be force to move from first compartment to second compartment or, from second to first compartment or in a cycle e.g. from one compartment to the other and then back to the original compartment.

Advantageous Effects

It is therefore the objective of the present invention to provide apparatuses that will combine the advantages and improve many of the above mentioned draw backs, and more specifically; 1). An apparatus for extraction that will handle multiple units as simple a single unit. 2). No individual engagement of units into holes of a manifold system. 3). Ready for use, no individual hermetic engagement of sub-units during the separation steps. 4). No centrifugation. 5). Each apparatus function independently from other units. (no shunt effect). 6). Integrated: volume control and flow rate control. 7). Optional incubation, multiple extraction or elution cycles. 8). A system that provides free access to the open compartment during the various steps of the protocol. Or to be used with pre-filled reagent cartridge. 9). Provide a system that is easy for automation. 10). Enable protocols which starts from original test tube, without initial pipetting step. 11). Provide an integrated unit for positive or negative extraction. 12). System suitable for used with magnetic beads, non magnetic beads, chromatography column, active disc, filter. These and other advantages will be manifested in specific embodiment description

DESCRIPTION OF DRAWINGS: BRIEF DESCRIPTION OF FIGURES

FIG. 1 shows an integrated device for extraction having upper open compartment, a lower closed compartment, and an intermediate compartment which is an extension of the upper compartment separated by an active disc barrier.

FIG. 1-1 demonstrates a detailed extraction protocol. FIG. 1-2 is a temperature profile of the extraction protocol of FIG. 1-1 and FIG. 1-3 is a protocol for negative extraction.

FIG. 2 is an isometric view of a chromatographic column as the active barrier.

FIG. 3 Isometric view of another embodiment , where the active solid support are paramagnetic beads placed in the upper compartment, the capillary tube has no filtering barrier.

FIG. 4 Isometric view of another embodiment, demonstrating negative extraction protocol, having a long capillary tube reaching the bottom of the lower compartment, and the active member are paramagnetic beads, a magnetic rod is applied at the lower compartment.

FIG. 5 isometric view of a modified device of FIG. 4, demonstrating negative extraction protocol, where the lower end of the extension tube has a passive filter, and active non-magnetic beads pre loaded into the lower compartment.

FIG. 6 is a schematic presentation of a full assay protocol using a device as in FIG. 2

FIG. 7-1 and FIG. 7-2 are isometric view of other embodiments, where the upper compartment is closed and the intermediate compartment is an elongated tube with no filtering barrier, the lower compartment is a regular tube having an upper open end.

Figure 1:
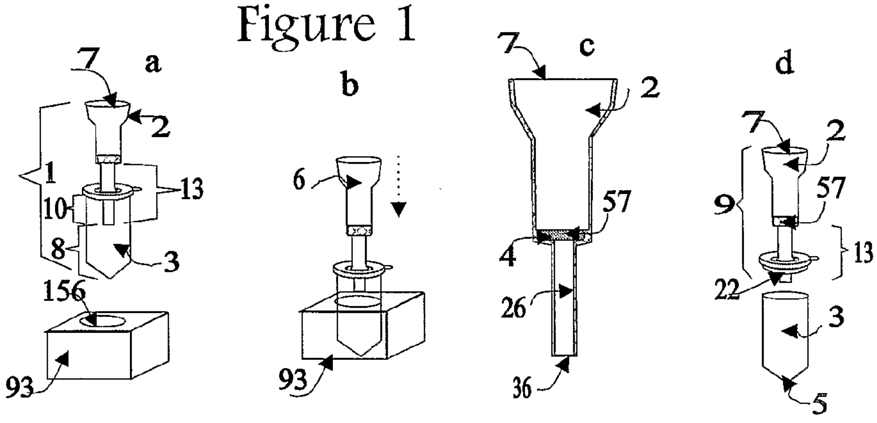
Figure 1:
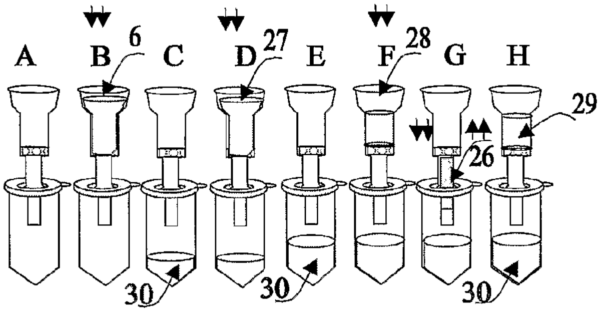
Figures 1, 2:
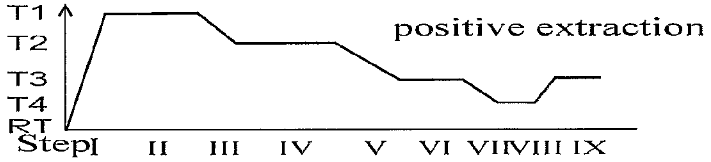

FIG. 7-1 shows magnetic rod applied at the upper compartment. FIG. 7-2 shows magnetic rod applied at the lower compartment FIG. 8-1 is an isometric view of an upward extraction assembly having upper closed compartment and lower open compartment, an intermediate long compartment having an active disc, showing an extraction cycle of a single unit. FIG. 8-2 is a isometric view of a positive extraction protocol of a strip of devices, and a set of pre-filled reagent cartridge related to FIG. 8-1.

FIG. 9-*a* an isometric view of another embodiment of the device where the intermediate tube extend in both sides, to form a one way collection zone in the upper compartment. FIG. 9-*b* demonstrates an upward positive extraction protocol (active disc at lower end). FIG. 9-*c* demonstrates positive extraction using magnetic particles.

Figure 10:
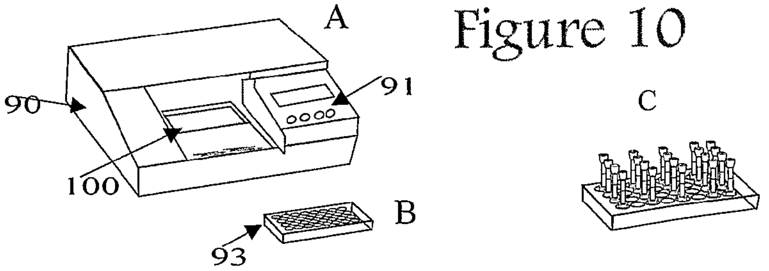
Figure 11:
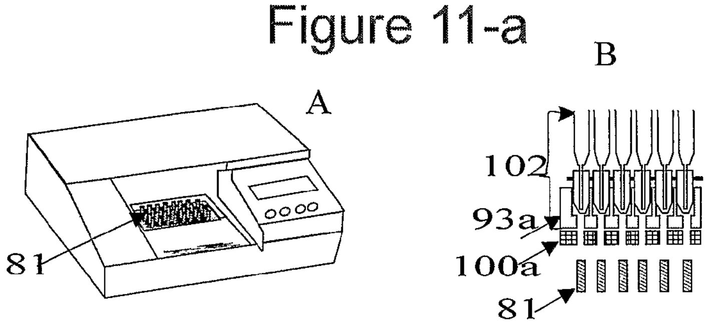
Figure 11:
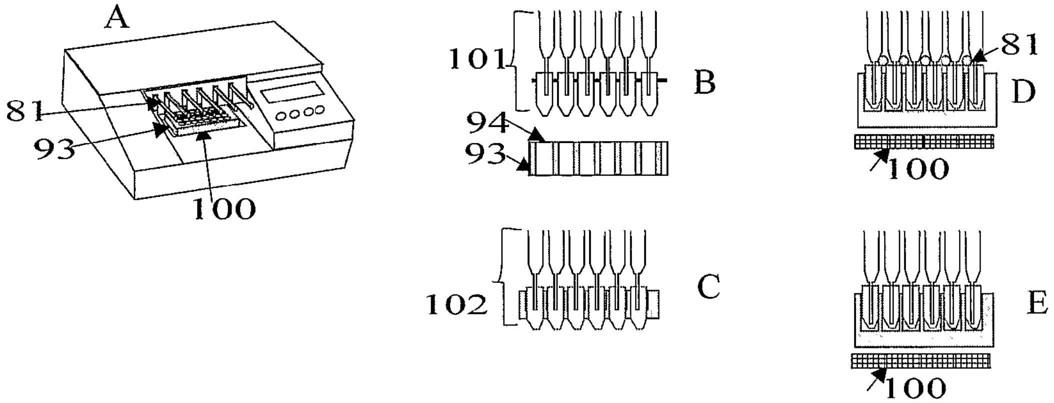
Figure 11:
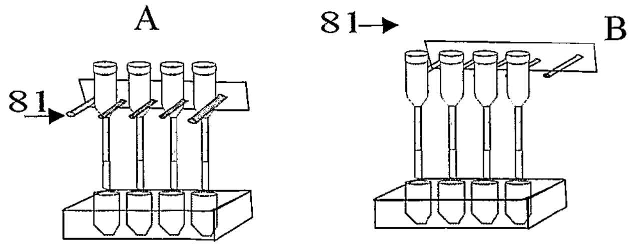

FIG. 10 is an isometric view of a thermoelectric unit for heating and cooling a heat block and FIG. 10-*c* is a heat block loaded with extraction units having a lower closed compartment FIG. 11-*a* is an isometric view of a thermoelectric unit, the unit also have movable magnetic rods for using with paramagnetic beads in the lower compartment. FIG. 11-*b* is an isometric schematic view of a thermoelectric unit with movable magnetic fork for using with paramagnetic beads in the upper compartment. FIG. 11-*c* is an isometric schematic view of the magnet fork member as in FIG. 11-*b*, in active relation (A) a nonactive relation (B) with the neck of the upper compartment.

FIG. 12 is summery of preferred embodiment and major characteristic of each embodiment Terms used: In this application we refer to some terms having specific meaning as follows:

Intermediate compartment; sometime referred as tube, capillary tube, moderate tube, barrier tube; all refer to a tube open at both sides, where the upper end is communicating with the upper compartment and the lower end communicate with the lower compartment. In different embodiments the intermediate compartment may have different function: a) a liquid retention volume, to store liquid, intermediate to sample and waste compartment, after passage through active barrier and temporary rest in this compartment. b) a restricted communication tunnel. c) a barrier which together with the closed compartment constitute an automatic valve.

Active solid support or active barrier: Solid support such as chromatographic column, absorbing filter, porous disc, coated paramagnetic beads, non magnetic beads, etc., capable of adsorbing or absorbing an agent or interacting with or retain at least one component of the sample.

Open compartment; a chamber which freely communicate with the ambient and has restricted communication with the closed compartment.

Closed compartment; a chamber which communicates with the ambient via the open chamber.

Waste compartment: a one way liquid collection closed compartment.

Heat cycle; Routine where the closed compartment is initially heated to a first temperature, then it is cooled to a second preferred temperature.

Cool cycle; Routine where the closed compartment is initially cooled to a first preferred temperature, then heated to a second temperature, where the second temperature may or may not be equivalent to initial temperature.

Two stage cycle; A stepwise heating or cooling cycle.

Negative extraction; Removal of at least one ingredient from a sample and collecting the purified sample.

Positive extraction; Extraction of at least one ingredient from a sample followed by washing and collecting the extracted ingredient.

Differential pressure; (dP); a state where the pressure in the closed compartment temporary differ from the pressure in the open compartment. Positive dP (+dP); dP in which the pressure in the closed compartment is initially made higher than that of the open compartment, by heating the closed compartment. Negative dP (−dP); Pressure differential in which the pressure in the closed compartment is initially lower than that of the open compartment, by cooling the closed compartment, upon the application of a “heating cycle” or a “cooling cycle” for a time sufficient to achieve a sufficient differential pressure, between the two compartments, the pressure in the closed compartment changes in response to temperature differential (dT), resulting in pressure differential, between the two compartments. As a result, fluid, be it liquid or gas will be transferred from one compartment to the other until reaching pressure equilibrium between the two compartments. Upon subsequent reversion of the temperature back to initial T, the differential pressure between compartments is reversed, and an equal aliquot of fluid, be it liquid or gas, will flow in reverse direction. When “cooling cycle” is applied, the resulting negative pressure differential (−dP) will cause an aliquot of fluid to flow from “open compartment” into the “closed compartment” through the barrier means, and then upon heating, there will result a positive pressure differential (+dP), and a fluid aliquot from the “closed compartment” will be transferred into the “open compartment” through the barrier means. The nature of the fluid that flows at each cycle depends on the configuration of the assembly.

Integrated volume control; The volume of the aliquot of fluid transferred is proportional to the temperature differential between the initial and final temperature, and the volume of the air pocket in the closed compartment. By adjusting the dT applied to the closed compartment, which in turn regulates the dP, the sample or only part of it can be moved from one compartment to the other. When processing multiple similar devices and similar sample volume, the volume of liquid that will move is the same for all the units. Although the method is performed simultaneously on many test devices, the dP within each device assembly is established independently of other units, thus avoiding shunt effect.

Integrated flow control; The integrated flow control mechanism greatly compensate the variability in flow characteristics of the barrier such as filter and column. this is so because dP in each device deteriorates in proportion to the volume of liquid already displaced at that point of time, this means that the fast unit will achieve initial higher flow rate, ahead of the others, but the transferred volume decreases the dP and as a result decreases the flow rate, so variation of flow rate between units is greatly reduced.

Improved efficiency; Extraction and elution steps can be repeated several times to improve efficiency of the process.

Incubation option; a stepwise cycle where the liquid temporary park for incubation and then proceed and accomplish the cycle.

Thermo member; Any external source that can heat and cool the air pocket of the closed compartment to a preferred temperature. Such as Thermo-electric module, IR, direct electric heating, and/or using gas, liquid, or other means for heating and cooling.

Thermo electric; A heating/cooling member based on Peltier TE module. Thermal block or Heat block; A removable metal block having cavities to accept at least part of the air pocket zone of the closed compartment, and is being heated and cooled by thermo member.

Best Mode

As one major advantage of the invention is that the platform can be used for executing various technologies, there is no single preferred embodiment, each technology has its own preferred structure, FIG. 12 is a summery of various preferred configuration for each methodology. The best of which are presented and explained in: FIG. 1, 2, 4, 7, 8

DETAILED DESCRIPTION OF FIGURES AND EMBODIMENTS

The versatility, advantages and the characteristics of the system will be demonstrated by some examples, it should be clear to a any one skilled in the art that other embodiments, modification of the given embodiment, as well as combination of embodiments or step of embodiments, or interrupting the protocol by applying other intermediate steps, such as centrifugation, incubation are all in the frame of this invention providing that they are within the scope of this invention.

FIG. 1—Example: Downward Extraction and Upward Elution.

Principle: In accordance with one preferred embodiment, the invention will be demonstrated using a device such as in FIG. 1 for positive extraction of an ingredient such as DNA out of a liquid sample using a solid support member, arrested at the interface between the upper and the intermediate compartment, the heat block is loaded with units and is preheated, a sample is added to the upper compartment, then the block is cooled, forcing the liquid downward, the supernatant of the extraction step is collected into the waste compartment (the lower compartment), while the DNA is extracted into the active solid support. Next, washing buffer is added to the upper compartment, the heat block is further cooled to suck the buffer so that the solid support is washed to remove impurities, and the waste is also collected in the lower compartment, then eluting buffer is added to the upper compartment and the thermal block is moderately cooled so that the eluting buffer will move to retention compartment, along the extension tube, but will not flow into the waste compartment, then forced back to the initial compartment, by heating the thermal block. The liquid collected in the waste compartment does not reach the level of the lower end of the intermediate compartment, thus will not be pushed up. All steps are accomplished in a single integrated device, and all liquid handling steps are done without the need to move the device and do not involve handling of the instrument, or replacing collection tubes, as is the case in centrifugation methodology and vacuum manifold.

Detail: The test device 1 of this embodiment (FIG. 1*a*), have a upper open unit 9 (FIG. 1*d*) and a lower closed unit 3, which is referred as a waste compartment in this embodiment, unit 9 comprises an open compartment 2 and a lower section 13 having a hermetically engaging closing cap 22 at the lower end and an active filter 57 at the upper end of an intermediate compartment 26, (FIG. 1*c*). When unit 9 is hermetically engaged to the lower compartment 3, the lower open end 36 of the intermediate compartment 26 rest above the level of liquid to be collected in the waste compartment. At least part of the collection compartment 3 contains entrapped air pocket 10, (FIG. 1*a*) and non-entrapped air pocket 8. The interface barrier 4 between the upper compartment and the intermediate compartment, comprise in this embodiment an active filter disc 57 such as silica membrane or ion exchange filter, or any other solid support known in the art. FIG. 1*c* is an enlarged, front cross section view (without the closing cap) of the upper compartment 2 having an open end 7 and a lower intermediate compartment 26 having a lower open end 36, compartment 2 and 26 communicate via an active barrier filter disc 57. The closed compartment 3 have an air pocket of which part is an exchangeable air pocket 8 defined in the region under the open end 36 of the intermediate compartment, this part of the tube serves mainly as a waste collecting zone. A second—non exchangeable (entrapped) air pocket zone 10 is located on top of air pocket 8 which serves mainly as an air spring. Compartment 26 serves as a communication channel in the steps of sample extraction and washing, yet serves as a volume retaining container during the elution step, to hold in a recoverable mode the eluting buffer. Which eluting buffer after downward elution step is hanging separated from the waste collected in the lower compartment and then the eluant is pushed back upward into the upper open compartment. This embodiment enables to execute a negative extraction (removal of interfering ingredient) as well as a positive extraction (extraction, washing and eluting an ingredient) protocol.

Example: Positive extraction: (FIG. 1-1) comprise the steps: A). Insert device 1 into the cavity 156 in of thermal block 93 (FIG. 10). B). Choose the program "Positive extraction" (FIG. 1-2). C). Add sample to each unit via open end 7 and press "enter". D). after a per-set time, add washing buffer via open end 7. E). after a per-set time, add eluting buffer via open end 7. F). after a per-set time the purified DNA is ready in the upper compartment.

More Detailed Description:

1) Providing a device 1 (or multiple devices) which is placed into the cavity 156 of a thermal block 93 (FIG. 1*a*, 1*b*) so that the entrapped air zone 10—is in good thermal contact with the thermal block 93. in one preferred method of operation which is given here as an example, the starting temperature RT shown as the first point in time-temperature profile FIG. 1-2. Thermal block 93 is attached to a heating-cooling source 100 (FIG. 10 A); the temperature and time of operation are regulated by common control means.

2) Raising the temperature of the heating block to T1, (step I in FIG. 1-2.) this increases the temperature of the air pocket to T1, a certain volume of air is pushed out of the device via intermediate compartment and via the barrier member (FIG. 1-1*a*).

3) Sample 6 is dispensed into the open compartment via opening 7 FIG. 1-1*b*, while the temperature is still at T1 (step II in FIG. 1-2) (if multiple samples are handled, dispensing step is repeated for each sample, into each device).

4) Temperature of the thermal member is reduced to T2, (step III) the air pocket in the closed compartment of each unit, be it one or many, will assume the reduced temperature of the thermal block, causing contraction of the air pocket, this establishes a negative differential pressure (−dP) between the open compartment and the closed compartments forcing the liquid sample from the open compartment to the closed waste compartment (FIG. 1-1*c*), via the active barrier, (At the end of each step, the pressure between compartments reaches new equilibrium.)

5) Washing buffer 27 is added via opening 7 FIG. 1-1*d*, while T is still T2 (Step IV).

6) T is lowered again to T3, (step V) causing a −dP, forcing the washing buffer from the open compartment to the closed compartment, the washing buffer is also collected as waste 30 in the lower closed compartment (FIG. 1-1*e*).

7) Elution buffer is added to the open compartment (step VI) (FIG. 1-1*f*).

8) T is further reduced to T4, (Step VII), T4 is regulated so that the elution buffer will penetrate only into the intermediate compartment 26, but not into the lower compartment, (FIG. 1-1*g*). If desired, incubation (step VIII) can be applied.

9) Raising the T to T3 or a little higher (step IX), the eluant containing purified ingredient, will be forced back to the open compartment (FIG. 1-1*h*), where it is ready for further steps.

This example demonstrates the bidirectional nature of the method; Initially, a volume V of air is pushed out of the (lower) waste compartment, then sample (v1) is being sucked into the waste compartment followed by washing buffer (v2) It is preferred that V is greater than v1+v2) alternatively, air can be pushed out (by heating) after sample or washing step to recharge the differential pressure potential, not shown in this example, and then an additional cycle of fluid flow is accomplished at the elution step.

One major advantage of this embodiment is that the positive extraction protocol including extraction, washing and elution is accomplished in a single and integrated unit, no need to replace collection tubes, thus saving disposables and handling time.

Another advantage is the free access to the open compartment, so that washing buffer and eluting buffer can easily be added manually or automatic. Another advantage is that the elution comprises a two pass step, i.e. the elution buffer releases the ingredient when force downward, and again when forced upwards, thus improves efficiency. These advantages make the system most suitable for manual and automation handling. Other advantages such as; simple handling of multiple units, no shunt effect, integrated volume and flow control, are as explained in next embodiments.

The diameter of the lower opening 36 and/or the diameter of the intermediate compartment 26 is limited so as hold the elution buffer hanging in the intermediate compartment and prevent it from dropping to the waste compartment, to ensure that the liquid will migrate upwards when a positive dP is established, the diameter should preferably be less than 6 mm.

Example: Negative extraction. (NE): The same device may be used for NE, i.e. to remove an interfering ingredient from a sample; this may be accomplished by using only part of the program:

a). Load device into the thermal block and insert into the instrument.

b). Choose the program "negative extraction".

c). Add sample to each unit.

After a preset time, NE is completed and the purified sample is ready in the upper compartment.

Detail: The protocol for negative extraction is given in FIG. 1-3: after preheating the air pocket (step I), a sample is added to the open compartment Step II), the temperature is moderately lowered, so that the liquid is forced down to the intermediate compartment (but not to the waste compartment), and by that a first extraction cycle is accomplished (step III), then the temperature is raised to push the liquid from the intermediate compartment back to the upper compartment (step IV), and by this step, a secondary extraction cycle is accomplished, and the purified sample is available in the upper open compartment. If desired, an additional cycle can be repeated (for instance, to remove residual impurities of the origin sample remained in the upper compartment.)

FIG. 2 presents a similar device as in FIG. 1 but the active barrier member 57 is a packed column. The column configuration have a significant void volume as compared to active disc, thus enable incubation step which may be needed when the extraction kinetics is slow.

Device 41 FIG. 2-*b*, comprise an assembly of two units; a waste collection unit 21 FIG. 2-*a* which may be a test tube having a closed bottom and an open upper end, and a sample—extraction-retaining unit 43, comprises an open compartment 2 having an open upper end 7 and a barrier member 57 comprising beads 56 in a column packed format.

FIG. 2*c* and FIG. 2*d* are perspective view of a multi (4 units) assembly prior to (FIG. 2*c*), and after being introduced into a heat block unit 93 (FIG. 2*d*), where the upper part of the closed compartments 3 are seated in the cavities and are in good heat contact with the heat block member.

In practice, the steps are similar to the steps in FIG. 1, with a modified program, to take in consideration the different volumes involved.

The steps as described are not mandatory, and may be modified to fit specific needs. Many such modified protocols are optional, which is another advantage of the present invention, for instance, when incubation step of the sample in the solid support is desired, step III may involve a reduced cooling step resulting in a smaller dP, and the liquid will initially be introduced into the solid support and not just passed through it, step IV can be extended to any preferred length of time, in order to improve recovery, washing buffer can now be applied to the open compartment, it will not mix with the sample as they rest in separated compartments, then in step V the dT can be a little larger than in previous example, in order to suck down the sum of volumes (sample then buffer), the washing step will be as effective, because the sample will propagate in the solid support in front of the washing buffer, The elution step can be done either by dry column method i.e. pre removing of washing buffer or by wet column method; Dry column: In order to remove any residual buffer from the column and intermediate compartment 26, extra (−dP) is applied at step V this will dry out the solid support, and than elution step is applied. Wet column; the elution buffer push the remaining washing buffer out of the solid support 56 into 26 and then when cooled, the eluant from 56 will move back to the upper compartment and buffer in 26 will be pushed into 56 zone. These manipulations are possible by choosing the preferred dT. It should also be clear to those familiar in the art, that the temperatures range must not be restricted to a region above RT and some or all steps may be executed at T lower than RT, as long as dT which generated the dP is correctly chosen.

Figures 1, 2, 3:
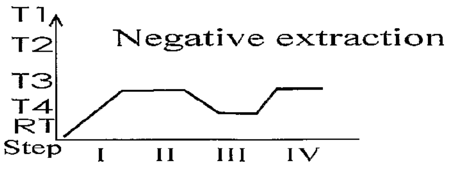
Figure 2:
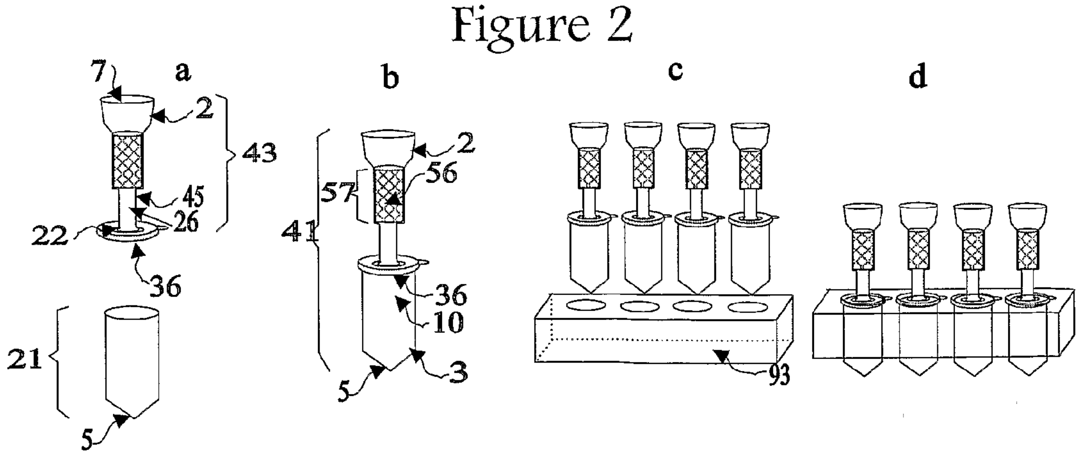
Figure 3:
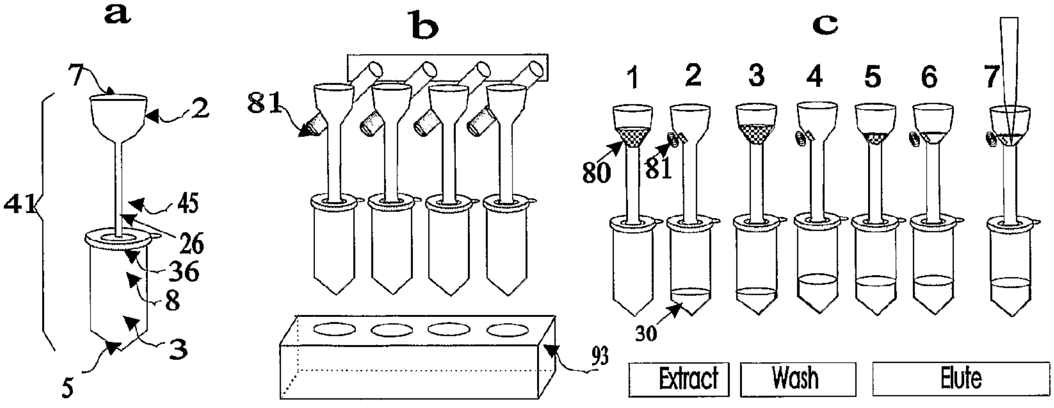

FIG. 3 Example: Suspension of Magnetic Beads in Upper Compartment.

Another embodiment of this invention demonstrate extraction of an ingredient—using magnetic beads as solid support, and a device (FIG. 3*a*) (having no filter barrier) comprising two part unit as described in FIG. 1 and FIG. 2, the device comprising: a lower closed compartment 3 and an upper open compartment 2 communicating via a capillary tube barrier 45, which capillary is hermetically engaged into the closed compartment, and the lower opening 36 rest just under the cap, the diameter of the capillary is preferably less than 4 mm, the entrapped air pocket. This embodiment have the advantage of waste collection compartment to spare aspirations steps In operation the method comprises the steps of: 1) insert the device (or devices) into the thermo block 93 so that the upper part of the lower closed compartment rest in the cavities of the thermo block (FIG. 3*b*), the block with the loaded devices is inserted into the instrument (FIG. 11-*b*), having movable magnetic rods 81, which can be moved toward (active mode) and away from (non active mode) the neck portion of the upper compartment and apply elevated T1. 2) into the open compartment add the sample, ingredients, magnetic beads 80 (FIG. 3*c*-1). The mixture with the magnetic particles 80 will remain in the upper compartment as long as there is pressure equilibrium between compartments. 3) Move the magnetic fork 81 to active mode (close proximity to the neck portion of the open compartment (FIG. 3 c-step 2). 4) Cool the thermo member to T2 (FIG. 3*c*-2), To move supernatant to waste compartment. 5) Move magnetic fork to non active mode, add wash buffer (FIG. 3*c*-3), magnetic beads mix with the buffer, and remain in the upper compartment as long as dP=0 relative to previous step. 6) Repeat step 3, 4 (FIG. 3*c*-4) (lowering the temperature to T3). 7) Repeat step 5 using eluting buffer (FIG. 3*c*-5). 8) Move the magnetic fork to active mode (FIG. 3*c*-6). 9) Remove eluant by pipette, while magnetic force is applied (FIG. 3*c*-7).

Figure 4:
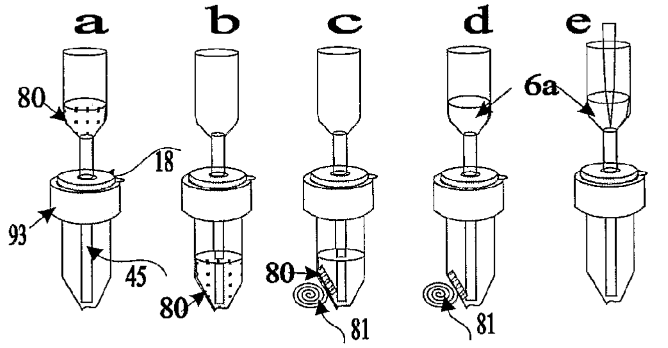
Figure 5:
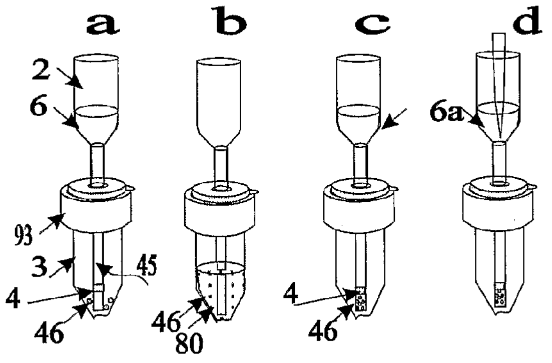

FIG. 4 Example: Negative Extraction by Magnetic Beads in Lower Compartment.

A device similar to the device of FIG. 3 but the capillary tube 45 is perturbing into the closed compartment 3 to reach the bottom of the closed compartment, with clearance to allow fluid flow. The capillary barrier has no filter member. This embodiment demonstrates the use of magnetic beads as solid support, which is captured in the lower tube, mixing is achieved by bubbling of air during cooling steps or by introduction of idle cycles. The magnet member is preferably a magnet rack 81 (FIG. 11-*a*). (The active position is indicated in the figures by spiral symbol 81)

In operation the method comprises the steps; 1) A device is placed into thermal block 93. 2) Sample 6, reagents, and magnetic beads are added into the upper open tube. (FIG. 4*a*). 3) The thermo block is cooled, to T1 (for example 100) this will suck mixture 80 down to lower compartment (FIG. 4*b*). 4) Next, magnet rack 81 is elevated to reach the bottom of lower compartment (FIG. 4*c*). 5) Next, heating to RT (for example 250) (FIG. 4*d*). The magnetic beads remain in the lower-closed compartment while the purified supernatant is moved to the open compartment (FIG. 4*e*). The heat block or the units may now be removed from the instrument, the purified sample will remain in the upper compartment, as long as the temperature remains constant. If preferred, an additional extraction cycle can be done by repeating steps 3 to 5. Major advantage-eluant may remain in the device, no extra tube needed for eluant collection FIG. 5—Example I: negative extraction, by active disc or column: A device similar in layout to device in FIG. 4, but contains a passive filter and non-magnetic active beads placed in the closed compartment. This embodiment is used for simple negative extraction of a sample and obtaining the purified liquid in the open compartment, as well as retaining the original volume of the sample after such removal is completed. The device of this embodiment comprises two compartments, an upper open compartment 2, a lower closed compartment 3, the two compartments communicate only via a capillary tube 45 having an porous disc 4 at lower end.

In operation: sample 6 is introduced to open compartment 2, via open end 7. The air pocket zone of the closed compartment is placed into a heat block which is then inserted into the thermo member of instrument 90 (FIG. 10) or wise versa. Reducing the temperature of the thermal member to (T2), the thermal shrinking of the air in the closed compartment generates a negative differential pressure (−dP) between the closed compartment, which response to the temperature change, and the pressure in the open compartment, which remains at ambient pressure, this −dP forces the liquid sample from the open compartment into the closed compartment to mix with active beads, the suspension can be mix periodically by applying idle cycles during incubation to accomplishing the extraction step. Next, the temperature of the thermo member is elevated back to T1, thus generating a (+dP), and the liquid which is at the bottom of the closed compartment, will be forced back into the open compartment, the beads will remain in the lower compartment, and the purified sample is collected in the upper open compartment.

The same device and method applies also when using an active disk or a packed column in the capillary tube. In operation: sample 6 is introduced to open compartment 2, via open end 7. The air pocket zone of the closed compartment is placed into a heat block which is then inserted into the thermo member of instrument 90 (FIG. 10) or wise versa. Reducing the temperature of the thermal member to (T2), generates (−dP) to force the sample into the closed compartment via the active barrier, and accomplishing a first extraction step. Next, the temperature of the thermo member is elevated back to T1, thus generating a (+dP), and the liquid which is at the bottom of the closed compartment, will be forced back into the open compartment, via the active barrier in the capillary tube, thus a second extraction step is accomplished, resulting in a more efficient extraction and removing interfering substances than in regular procedures where only one extraction pass is accomplished.

FIG. 6 Example: Eliza: bidirectional flow embodiment: By another embodiment of the method of the invention, the example demonstrates a more complicated protocol such as assaying component in a liquid sample.

In accordance with this embodiment, the method proceeds in a similar manner as in FIG. 1, 2 described above but comprise additional steps and aspect of processing and detecting a signal from the open and/or closed compartment. The signal may be one emitted from a signal molecule which was apriori bound to said component; it may be emitted from a signal molecule which is capable of binding to said component and introduced into the open compartment at a suitable time; it may be a signal emitted from a signal molecule which competes on binding sites on said active solid support particles with said component; and may be a signal formed as a result of an enzymatic reaction between enzymes directly or indirectly bound to said compartment.

A particular example of the above embodiment is the performance of an ELISA test. ELISA method in this example will be demonstrated by "sandwich" methodology-known in the art. The sandwich assay is based on solid support to which a specific antibody is attached, (active solid support), the sample containing the agent is incubated with the active solid support (Ib), the unbound agent is removed by washing step (IIb), followed by incubation with an enzyme-linked specific antibody (Ab-Enz) to the bound agents (IIIa, IIIb) which enzyme-linked antibody may either be an antibody against said agent or an antibody directed against another antibody which is directed against said agent. Next the unbound Ab-Enz is washed off (IVa, IVb), and substrate is added to the bound solid support (Va), followed by reading the signal.

More Detailed;

Providing a device 1 (or multiple devices-not shown) which is placed into a thermal member 93 (FIG. 1*b*) so that the entrapped air zone is in good thermal contact with the thermal member 93. In one preferred method of operation which is given in here as an example, the starting temperature T0 is RT, shown as the first point in time-temperature chart FIG. 6-1.

Step 1 (FIG. 6-1.)—The temperature of the heating block is initially raised to relatively high temperature T1, (for example 90 degree C.) this establishes a positive (dP), an aliquot of air is pushed out of the device via intermediate compartment and via the barrier member. Step 2—While the temperature is at T1 (for multiple samples, dispensing step is repeated for each sample) sample 6 is added into the open compartment (FIG. 6 I a). Step 3, the temperature is reduced to T2, the air pocket in the closed compartment of each unit, be it one or many, will assume the temperature of the thermal member, and hence the (−dP) is forcing the liquid sample to the closed compartment (FIG. 6 Ib), via the active barrier. The volume that is being sucked is regulated by choosing the preferred temperature. Step 4—While T is still T2, washing buffer 27 is added to the open compartment—FIG. 6IIa. Step 5—reducing the T to T3 to accomplish the washing step. Step 6—an active reagent Ab-Enz, 70 is dispensed into upper compartment, FIG. 6IIIa. Step 7—reducing T to T4, T4 is adjusted so that the AB-Enz buffer will penetrate into the active barrier only, to enable incubation. Steps 8, 9; washing step (as in 5, 6) is repeated (FIG. 6IVa), which involves the reduction of T to T5. Step 10, a substrate 71 is added (FIG. 6Va) into the upper compartment. Step 11 T is reduced to T6, regulated so that the substrate buffer will only penetrate into the active barrier, to enable incubation. Next T is raised to the T5 region, and the sample with the signaling molecule 72 is pushed back to the open compartment (FIG. 6Vc), ready for further analysis.

Internal control: One possible modification of the protocol is to increase the volume of the substrate 71 to be more than is needed for the incubation in the active barrier, the excess will flow into the collection zone 30, and as this waste pool 73 contains most of the AB-Enz from step VII, VIII, IX, the excess substrate will react with the Enz, a strong control signal is generated in the closed compartment.

FIG. 7 Example: Extraction by Magnetic Bead from a Sample in a Test Tube:

This is another embodiment of the present invention and is demonstrated by an examples and how the same device can be used in two different methodologies, the device comprises an upper closed compartment having a long extension tube barrier, whit no filter, demonstrates extraction of an ingredient—from a test tube using active magnetic beads and a magnetic force applied at; the neck of the upper compartment (FIG. 7-1) or at the lower compartment (FIG. 7-2).

FIG. 7-1: Magnetic beads and magnetic fork at upper compartment. The device comprises (FIG. 7-1*a*): an upper unit 42 comprising a closed compartment 3 and an lower open compartment 2 communicating via a capillary tube barrier 45, which capillary is an extension of the closed compartment, the lower opening 36 rest at bottom 5 of an open compartment 2, no filter barrier is involved in this embodiment so as to allow free flow of cells, debris and alike, the diameter of the capillary 45 should be less than 6 mm and more preferably, less than 4 mm. The air zone of the closed compartment is inserted into the thermal block 93, and the capillary tube is immersed into the open compartment containing a mixture of sample and magnetic beads (optionally lyses buffer), with clearance to allow fluid flow. During incubation period, the suspension can be mixed by idle cycles. The magnetic force is applied using a magnetic fork 81 (as in FIG. 3-*b*), which become active at close proximity to the neck portion of the close compartment (the active mode is indicated by symbol 81). The open compartment 2 in this embodiment is a set of pre-filled tubes (cartridge), the open compartments of the cartridge are so arranged, to match the arrangement of the magnetic fork and cavities in the heat block. The closed compartment may also have a downward skirt to reach and protect the lower open compartment from aerosol (not shown).

Example: (FIG. 7-1) Direct Isolation of Nucleic Acid from Cells using Magnetic Beads.

In operation the method comprises the steps;

1) the sample is lysed in the tube, and then active magnetic beads are added (total volume-100 micl). 2) The device 42 (2 ml total capacity, and 1 ml air pocket volume) is placed into thermal block 93 so that the closed compartment is in the thermal zone and capillary tube 45 is inserted into mix 80. 3) The thermo member is heated to initial high temperature T1 (for example 60 degree C.). A positive differential pressure (+dP) is established and an aliquot (140 micl) of air is displaced out of the compartment 3, via the sample mixture, this bubbling through the sample contributes to the mixing of the beads and improves the capturing step, the rate of bubbling can be controlled by the rate of heating. This build-in mixing capacity also simplifies this step for automation. (it is also optional to insert tube 45 after pre heating to T1, to avoid bubbles). 4) Reducing the temperature to T2 (example; 30 degree C.) to generate a negative −dP, which sucks the mixture 80 into the upper compartment-via the capillary tube. 5) Activating the magnet 81, by moving the magnet to the neck portion of the closed compartment 3. (FIG. 7-1*c*) at this position the temperature is kept constant to allow the magnetic beads to be attracted toward the wall of the neck. 6) Heating to T2 (80 degree C.) (FIG. 7-1*d*) the magnetic beads are retained in the upper compartment while the purified sample is pushed back to the open compartment. 7) Tube 2 is removed for downstream applications. If desire, steps 3-6 can be repeated to rinse sample leftovers in the tube.

A positive extraction protocol is accomplished by replacing the open tube with washing buffer tube and than by elution buffer tube and repeating the steps as described.

FIG. 7-2 Example: Removal of Impurities by Magnetic Beads at Lower-Open Chamber.

FIG. 7-2 demonstrates extraction of an ingredient using active magnetic beads and a device as in FIG. 7-1*a* but using a magnet rack at the bottom of tube 2. In operation the method comprises the steps of: 1). Repeat step 1 to 3 of FIG. 7-1. 2). Activate the magnetic tray at the bottom of the open compartment. 3). Cool to T2, this will suck the fluid to the upper compartment, while the magnetic beads are retained at the bottom of the open tube. (FIG. 7-2*b*). 4). Replace the open tube with a new one (FIGS. 7-2: *c*-1 and *c*-2). 5). Heat to T1, the purified liquid will be forced back to an open compartment. (FIG. 7-2*d*).

FIG. 8; Example: Extraction, using an Upper Closed Compartment and Active Porous Disc.

In accordance with this embodiment, the unit (FIG. 8-1*a*) is similar to the unit in FIG. 7 but has an porous disc 56 (active) placed along the capillary tube or passive disc and non-magnetic beads in the upper compartment. In practice: FIG. 8-1 *b* to *d* demonstrates liquid position of one cycle, FIG. 8-1*b* describes an assembled unit where liquid sample is already placed in the lower compartment. 1). The extraction unit 42 is inserted into the thermal block 93. 2). The closed compartments are pre heated to T1 (i.e. 80 degree C.), the sample tube is introduced so that the capillary 45 is immersed into the liquid-down to the bottom (assembly 50), (FIG. 8-1*b*). 3). Applying "cooling mode" by cooling to T2 (i.e. 50 degree C.), fluid 6 is forced from the open compartment 32 into the closed compartment 33 via the active barrier 56, (FIG. 8-1*c*). Upon reverting the temperature in the thermal block back to T1, generating a +dP, the liquid is forced back in to the bottom of the original open compartment, (FIG. 8-1*d*). This cycle (I) is repeated after replacing the open tube with a tube containing wash buffer (II), and once again when the tube is replace with a new tube containing elution buffer, (III).

One advantage of this embodiment is that samples that are already in a well or tube can be processed, without the need of sample pipetting. Another advantage is that extraction step involves a double pass of liquid through the solid support, thus improving recovery. In order to improve recovery more, the cycle step FIG. 8-1*a* may be repeated, this will extract some more ingredient, such as leftovers on the walls of the open tube.

FIG. 8-2*e* present a strip of wells and the exchange of strips to accomplish an extraction protocol: I-extraction cycle, II-washing cycle, III-elution cycle. Cycle I can be used for negative extraction protocol. Cycle I+II+III is used for positive extraction protocol.

FIG. 9 Example: PE from test tube by upward extraction and downward elution. FIG. 9*a* presents another embodiment for positive extraction of an analyte, performed directly from a test tube containing the sample. The open compartment in this embodiment is the tube or a well containing the sample. This embodiment uses a combination of protocols, first protocol is to enable collection of waste liquid in the one way collection zone at the upper closed compartment, a second protocol is to recover the desired fraction back into the open compartment or inspect the eluted fraction in the capillary tube. The test device 42 of this embodiment, is having an upper closed compartment 3 communicating with the ambient via a communication tube 13 containing an active barrier member 56, which barrier member 56 in this embodiment, is positioned at the lower end of the capillary tube, while the upper part 12 of the extension capillary tube is perturbing into the closed compartment, which upper end of the capillary tube is, preferably in close proximity to the cap 18, the extension tube 13 serves as a communication tube in some parts of the protocol and as a volume retaining intermediate tube 26 in other parts of the protocol. The lower part 11 of the closed compartment 3, which coincides with the perturbing extension tube, serves as a one way collection zone, and initially contains an exchangeable air pocket 10, and on top of it, an entrapped air pocket 8.

In operation, demonstrated by a single device at different stages of the protocol, the method comprises the steps; (FIG. 9-*b*). 1). The upper end of device 42 (or multiple devices) is placed into a thermal block 93 which is adjusted to heat the air pocket zone 10, which is heated to initial high T1 (for example 80 degree C.) (Step I-in flow chart FIG. 9-*c*). A (+dP) is established, and an aliquot of air is displaced out of the compartment 3. 2). Sample 6 is introduced to open compartment 2, which is then placed under the capillary tube, and the lower end of the capillary tube is immersed into the liquid in the open compartment. 3). cooling to T2 (for example 70 degree C.) (Step III in flow chart) to generate (−dP), which sucks an aliquot of liquid sample from the open compartment into the active zone, dT is so adjusted as to correspond to the suction of total sample volume. 4). Keeping temperature constant for incubation time and adding wash buffer 27 to the empty tube 2 (Step IV in flow chart). 5). Cooling the closed compartment to T3 (50 degree C.) (−dP) to force the buffer into the waste collection zone 11 of the closed compartment, via the solid support (Step V in chart). 6). Elution buffer 28 is added to the open compartment 2, (FIG. 9-*b*6). 7). The temperature is further cooled to T4, (for example 40 degree C.) i.e., T4 is so adjusted to force the liquid only into the capillary compartment 26, but not into the collection zone 11 (step VII). (FIG. 9-*b*7 shows the purified fraction 29 in capillary tube 26). 8). Reverting the temperature back to T3 or to a higher preferred T, where the liquid 29, containing now the extracted ingredient, will be forced back to the open compartment, resulting in purified ingredient 29 in the original tube. This step has also another advantage; as the elution buffer is passing the solid support twice, (once in the way up and second time on the way back) thus increasing recovery. The sub units must be disengaged at this stage i.e. removing the lower-open compartment-containing the eluted ingredient, so that when the upper closed unit 3 will cool down spontaneously or deliberately, the elution liquid will not be sucked up again. Dashed line in FIG. 9-*c*; It should be clear to those familiar in the art that other temperature profiles are possible, for instant the dashed line in the flow chart, where at step IV the T is raise again to T1 and then proceeded as explained (this is useful when larger volumes are to be handled, or when drying the solid support is advantageous). it should also be clear that when forcing the eluant downward, devices other than the test tube may be used, and by stepwise increasing of the temperature, small aliquots can be dispensed and distributed FIG. 9-*b* Eliza protocol: Eliza protocol may be accomplished by using a similar protocol with the appropriate modification; for example, following the extraction and washing step as explain, an antibody-enzyme conjugate is added, and the thermo member is cooled to absorb the liquid into the active zone and incubating at that temperature, washing step is repeated, followed by adding a substrate solution which is absorbed by further moderate cooling, so as to keep the liquid in the capillary tube, and after incubation time the signal may be monitored in the capillary tube, or the thermo member may be heated to force the liquid back into the open compartment.

FIG. 10 and FIG. 11: Thermal member: in this invention relates generally to any mean capable of heating and cooling, at reasonable rate, and transmit the desired temperature directly to a defined zone of the device, or to a thermal block having integrated cavities for a single or multiple devices, which cavities are designed to be in good thermal contact with the air pocket zone of the device, the supply maybe either from one source (as in Peltier) or by alternating sources such as heating and cooling fluid sources that are interchangeable according to a specified program. The instrument may preferably be programmable and controlled by regular technology known in the art. The instrument may also contain or be synchronized to pipetting and and/or aspiration station. The instrument may also contain or be synchronized to a magnetic member such as magnetic plate, vertical (Z) movable multi magnetic rods (pistons) or horizontal magnetic fork, preferably moveable in XZ coordinates etc., It is preferable that the air zone of the devices be of thin material to improve thermal conductivity. It is also preferable that the liquid zone be at a non thermal conductivity zone in the cavity.

FIG. 10 describes an instrument for carrying out embodiments where the closed compartment is the lower compartment, FIG. 10 is a schematic isometric view of a basic thermo electric instrument 91, for non magnetic separation, having a Peltier module with a conducting surface 100 for positioning a thermal block 93 (FIG. 10*b*), which thermal block is an interchangeable metal block with wells 94, part of which are occupied with devices in this example (FIG. 10*c*). The number of devices loaded may be one up to the number of cavities in the thermal block, no other steps are necessary (such as bucket balancing in centrifugation, or dummy stopper in vacuum manifold). The loaded thermal block is placed on surface 100, and extraction according to one of the relevant protocols may be executed. Cavities of heat block are so shaped so that only the air pocket zone is thermal contact. with the block, the shape of cavities may be a pass trough holes so that the con shaped lower tube is not in contact with the liquid zone, to avoid direct heating of liquid in the lower compartment. Instrument 90 have a control center 91 and preferably be programmable either by internal hardware or by reading from an outside source.

FIG. 11-*a* (A) is all instrument as in FIG. 10 and also comprise movable magnetic pistons 81, to be used for magnetic separation, where the lower compartment is closed and where magnetic beads are to be captured in the lower compartment. FIG. 11-*a* (B) is a front cross section view of the inter relation of the components:

A device as in FIG. 4 (6 units (102) in this figure) is loaded into a thermo block 93, which is then placed over thermo member 100*a* of the instrument, where the thermo member plate 100 has a set of holes (100*a*) to enable up and down movement of magnetic rod 81. Which magnetic fork 81 can be manually operated or synchronized with the heating cooling unit so as to activate and deactivate by the program. Thermo block 93*a* is similar to heat block 93 and contains a set of matching holes to enable the magnetic rod to reach good proximity to the bottom of the lower compartment.

FIG. 11-*b* (A) describes an instrument similar to the instrument described in FIG. 10 and have also moveable magnetic fork 81 which magnetic fork 81 can be manually operated or synchronized with the heating cooling unit so as to activate (close proximity to separation zone) or deactivate interaction with paramagnetic particles as described for instance in FIG. 3. FIG. 11-*b* (B,C,D,E) are front cross section views of the inter relation of components at various stages. FIG. 11-*b* (B) is a front section view of a set of 6 units (101) to be inserted into the cavities 94 heat block 93. FIG. 11-*b* (C) is a front cross section view of the loaded block (102). FIG. 11-*b* (D) is a front cross section view of 102 placed into the instrument over the thermo member plate 100 and the magnetic fork is in active position (at the neck of the upper opened compartment. FIG. 11-*b* (E) is a front cross section view where the magnetic fork is in a non active position. FIG. 11-*c* (a) is an isometric schematic view of FIG. 11-*b* (D), where the position of the magnetic fork is in active mode at the neck portion of the upper compartment. FIG. 11-*c* (b) is an isometric schematic view of FIG. 11-*b* (E), where the position of the magnetic fork is in none-active mode, away from the neck portion of the upper compartment. (lower or away)

Other heating/cooling embodiment of the instrument useful to carry out the method according to the invention may be used, such as regulated air blowing, light source or a combination of such elements, preferably in the range of 0 to 95 degree C. with air distribution mechanism to achieve good thermal convection with the closed compartments of the assembly.

The invention claimed is:

1. An apparatus adapted to extract an ingredient from a liquid by bi-directional transferring of an aliquot of fluid therein, said apparatus comprising:

an open compartment having a bottom end, an open end, and wherein said open compartment is adapted to apply reagents and remove purified liquid, wherein said open compartment is operable at a substantially constant ambient pressure;

a closed compartment having a closed pressure and having a closed end, a communicating end, said closed compartment having a bottom zone adapted to at least temporarily retain a fraction of said aliquot of fluid, and an upper zone containing an air pocket adapted to generate internal positive and negative pressure;

an intermediate transferring-retaining compartment having an intermediate compartment volume, a first end communicating with said open compartment, and a second end communicating with said closed compartment, said intermediate compartment is adapted to at least temporarily retain a fraction of said aliquot of fluid, wherein said open compartment is reversibly communicating with at least one of said temporary retained fluid fractions; and a flow barrier member, configured between said open and closed compartments and operable with said closed compartment and adapted to inhibit a flow of said aliquot of fluid when said closed pressure is substantially equal to said ambient pressure and to allow said flow of fluid when said closed pressure is substantially different from said ambient pressure, the pressure differential controllable by an external thermo member adapted to alternately change the closed pressure by a cool and a heat cycle, wherein at least one aliquot of fluid is alternately transferrable back and forth said open compartment in response to changes of the closed pressure.

2. An apparatus as in claim 1 where said barrier member comprises a restrictive flow zone chosen from the list including: a filter means; a porous disc; a bore; a capillary tube; and a combination of said restriction means.

3. An apparatus as in claim 2, wherein said barrier member additionally comprises an active solid support adapted to interact with said ingredient, said active solid support having at least one characteristic chosen from the list including: chemically active; linked; and coated with a reactive ingredient chosen from the list including: an antibody; an enzyme; an ion exchanger; an absorption reagent; an oligonucleotide; a receptor; and a lectin.

4. An apparatus as in claim 3, wherein said open compartment is configurable substantially above said closed compartment with said second end positioned within said closed compartment and displaced from said bottom zone wherein fluid in said bottom zone is an irreversibly waste collection zone; said active solid support positionable substantially at said first end, where said intermediate compartment volume is adapted to temporarily retain a specified volume of said liquid and wherein said temporarily retain liquid is adapted to reversible flow back into said open compartment or to waste collection zone.

5. An apparatus as in claim 3 wherein said closed compartment is configurable substantially above said open compartment and said bottom end is closed, wherein said first end is insertable within said open end and said first end is displaced from said bottom end to allow fluid flow and wherein said active solid support is positionable at said second end.

6. An apparatus as in claim 3, wherein said open compartment is configurable substantially above said closed compartment with said second end positioned within said closed compartment, substantially at said closed end, and said active solid support is positionable substantially at said first end.

7. A method for extracting an ingredient from a liquid sample comprising the steps of:

providing an apparatus comprising:

an upper open compartment and a lower closed compartment;

an intermediate communication- retention compartment extending from the bottom end of said open compartment, where the opposite end of said intermediate communication- retention compartment communicating with said closed compartment and adapted to rest above a specified volume adapted to serve as a waste collection zone in said closed compartment;

a flow barrier positionable in the path of fluid flow;

an extraction zone positionable approximately at the upper section of said intermediate compartment, where said intermediate compartment is adapted to have a specified volume and where said air pocket rests above said waste volume, wherein said barrier member together with said closed compartment are adapted to prevent the flow of fluids through said barrier member under conditions of substantially equal pressure between said closed and open compartments and allowing said flow under conditions of pressure differential (dP), which dP controlled by an external source member, wherein said open pressure is constant and equivalent to an ambient pressure, which external source member comprises an external thermo member zone adapted for heating and cooling said air pocket, wherein the volume of the transferred fluid correlates with the change in temperature dT and to the volume of the air pocket in said thermal zone, generating an internal dP by either heating or cooling said air pocket zone;

applying a positive differential pressure by heating said air pocket zone to a higher preferred temperature where the pressure in said closed compartment becomes higher than the ambient pressure, thereby forcing fluid, be it liquid or air, to flow out of said closed compartment; or applying a negative differential pressure by cooling said air pocket zone to a preferred lower temperature, wherein the pressure in said closed compartment become lower than the ambient pressure, whereby fluid is forced into said closed compartment; or applying a sequence of said positive dP and said negative dP to define a heating cycle to force fluid flow out of the closed compartment and then force said fluid in the opposite direction; or a sequence of said negative dP and said positive dP to define a cooling cycle to accomplish a bi-directional fluid transfer; and further including the steps of:

I extraction:

a) inserting said air pocket zone into the said thermo member zone preheated to an elevated T, b) charging sample into said open compartment, c) applying a stepwise cooling cycle by first cooling to temperature T5, whereby the liquid is force into the extraction zone, d) incubating at T5 and then applying further cooling temperature T4 to suck the sample further into said waste collection zone;

II washing:

a) charging washing buffer into said open compartment, b) cooling to T3 to suck the washing buffer into waste collection zone; and, III eluting:

a) charging elution buffer into said open compartment, b) applying a moderate cooling cycle; by cooling to T2 so that the liquid will pass the active extraction zone only to remain in said intermediate tube, and avoid dropping into said closed compartment, and c) heating to T3 whereby the liquid in said intermediate tube is forced back and the eluent is collected in said upper open compartment.

8. A method according to claim 7 for the detection of an agent in a liquid sample, said method comprising the steps of:

binding using said extraction step I, washing using said washing step II, binding at least a second ingredient, by charging a second ingredient solution into said open compartment and repeating said step I, repeating said step II, providing a signal component by:

a) charging a substrate buffer into said open compartment, b) cooling to a preferred temperature to suck said substrate buffer into said active zone in said intermediate compartment, and incubating, and c) reverting to original temperature, whereby the liquid with said signal component is forced back to said upper open compartment.

9. A method according to claim 7 for extracting a component from a liquid sample, further comprising the steps of:

providing an apparatus comprising:

an upper closed compartment, having an extension tube at a bottom end, a lower open compartment having a closed bottom end; and an upper open end, wherein said capillary extension tube extends to the bottom of said second open compartment adapted to allow fluid flow; and wherein said active extraction zone rests in the path of fluid flow, an air pocket is entrapped in said closed compartment, and said barrier member is disposed in the path of fluid flow; and inserting said air pocket zone of said upper closed compartment into said thermo member zone, and applying;

a) an extraction cycle;

b) a washing cycle, by transferring said extraction unit to a new open compartment containing washing buffer and applying said cooling cycle; and c) an elution cycle, by transferring said extraction unit to said new open compartment containing elution buffer and applying said cooling cycle.

* * * * *